(12) United States Patent
Guo et al.

(10) Patent No.: US 10,793,510 B2
(45) Date of Patent: Oct. 6, 2020

(54) METHOD FOR PREPARING ARYL SUBSTITUTED P-PHENYLENEDIAMINE SUBSTANCE

(71) Applicant: Sennics Co., Ltd., Shanghai (CN)

(72) Inventors: Xiangyun Guo, Shanghai (CN); Jinguo Xing, Shanghai (CN); Xiaomin Ruan, Shanghai (CN); Xinmin Chen, Shanghai (CN)

(73) Assignee: Sennics Co., Ltd., Shanghai (CN)

( * ) Notice: Subject to any disclaimer, the term of this patent is extended or adjusted under 35 U.S.C. 154(b) by 0 days.

(21) Appl. No.: 15/956,618

(22) Filed: Apr. 18, 2018

(65) Prior Publication Data
US 2018/0237376 A1    Aug. 23, 2018

Related U.S. Application Data

(63) Continuation of application No. PCT/CN2016/070614, filed on Jan. 11, 2016.

(30) Foreign Application Priority Data

Oct. 21, 2015  (CN) .......................... 2015 1 0691388

(51) Int. Cl.
*C07C 209/60* (2006.01)
*C07C 209/68* (2006.01)
*C07C 211/55* (2006.01)

(52) U.S. Cl.
CPC .......... *C07C 209/60* (2013.01); *C07C 209/68* (2013.01); *C07C 211/55* (2013.01); *C07C 2523/38* (2013.01); *C07C 2601/16* (2017.05)

(58) Field of Classification Search
None
See application file for complete search history.

(56) References Cited

U.S. PATENT DOCUMENTS 3,219,704 A * 11/1965 Verth James ......... C07C 209/68
                                                              564/398
4,431,841 A *  2/1984 Malz, Jr. ............... C07C 209/26
                                                              564/398
4,804,783 A      2/1989 Nagata et al.
5,536,878 A      7/1996 Nagata et al.
8,575,392 B2    11/2013 Yoshimoto et al.

FOREIGN PATENT DOCUMENTS

| CN | 102584596    | * | 7/2012  |
|----|--------------|---|---------|
| JP | S-5758648 A  |   | 4/1982  |
| JP | S-60193949 A |   | 10/1985 |
| JP | S-60202846 A |   | 10/1985 |
| JP | H-06192187 A |   | 7/1994  |
| JP | H-07215920 A |   | 8/1995  |
| JP | H-07278065 A |   | 10/1995 |

OTHER PUBLICATIONS

Acid entry from the Academic Press Dictionary of Science and Technology, downloaded from https://search.credoreference.com/content/entry/apdst/acid/0 on Aug. 27, 2019 (Year: 2019).*
Wang, Wei et al., "New Synthesis of Phenyl/Phenyl End-Capped Tetraaniline in the Leucoemeraldine and Emeraldine Oxidation States," Synthetic Metals, vol. 129, No. 2, pp. 199-205 (Jul. 10, 2002).

* cited by examiner

*Primary Examiner* — Amy C Bonaparte
(74) *Attorney, Agent, or Firm* — Mei & Mark LLP; Manni Li

(57) ABSTRACT

A method for preparing an aryl substituted p-phenylenediamine substance is provided. A structural formula of the aryl substituted p-phenylenediamine substance is shown as Formula (I'), where each of R' and R" is phenyl or o-methylphenyl, and R' is same as or different from R"; and the method comprises that: a raw material A and a raw material B are reacted in the presence of a hydrogen acceptor and a catalyst to form the aryl substituted p-phenylenediamine substance, the raw material A having a structure shown as Formula (I), the raw material B being cyclohexanone and/or o-methylcyclohexanone and the hydrogen acceptor being a hydrogen acceptor capable of accepting hydrogen for conversion into the raw material B. Raw materials are low in cost and readily available; use of a large amount of water for post-treatment is avoided. The reaction condition is relatively mild, and corrosion to equipment is avoided.

8 Claims, No Drawings

METHOD FOR PREPARING ARYL SUBSTITUTED P-PHENYLENEDIAMINE SUBSTANCE

CROSS-REFERENCE TO RELATED APPLICATIONS

The subject application is a continuation of PCT/CN2016/070614 filed on Jan. 11, 2016, which claims priority on Chinese Patent Application No. 201510691388.9 filed on Oct. 21, 2015 in China. Both PCT international application and Chinese priority application are incorporated herein by reference.

TECHNICAL FIELD

The present invention relates to the technical field of organic synthesis, and particularly, a method for preparing an aryl substituted p-phenylenediamine substance.

BACKGROUND

An aryl substituted p-phenylenediamine substance is an important class of p-phenylenediamine derivatives that is a compound or mixture (called as a mixture because it may comprise different compounds and these compounds have the same parent nucleus structure but different substituted aryls), and is prepared by performing aryl substitution on an N-amino hydrogen atom and N'-amino hydrogen atom in p-phenylenediamine. A rubber antidegradant 3100 is an important one in the class of aryl substituted p-phenylenediamine substance.

The rubber antidegradant 3100, with a chemical name of N,N'-dimethylphenyl p-phenylenediamine or diaryl p-phenylenediamine, includes three compounds with different structures, and structural formulae of the three compounds are as follows, respectively:

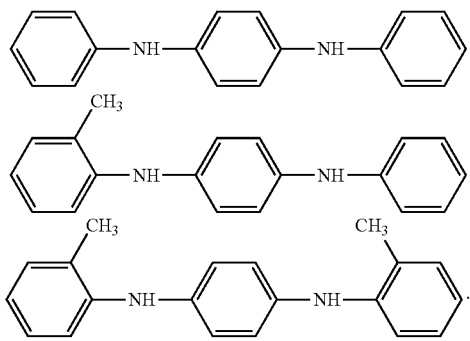

The rubber antidegradant 3100 is a typical delayed action type p-phenylenediamine rubber antidegradant. It may effectively overcome the shortcoming for present dominant p-phenylenediamine antidegradants 4020 and 4010NA, which have good early aging inhibition effects but slightly poor post aging inhibition effects. The rubber antidegradant 3100 is applied to natural rubber and synthetic rubber, such as cis-butadiene rubber, styrene-butadiene rubber, nitrile butadiene rubber, and chloroprene rubber, and belongs to a variety of efficient antidegradants with extremely good ozone-resistant protection effects for tires.

At present, a main production process for a product is as follows: p-dihydroxybenzene, aniline, and o-toluidine are taken as reaction raw materials, and are reacted in a normal-pressure or high-pressure kettle in the presence of a Lewis acid (for example, anhydrous ferric chloride) catalyst. In the process, toluene is adopted as a water entraining solvent to continuously entrain water produced by the reaction out of the reaction system to promote the reaction to be performed towards the direction of producing the product. A reaction temperature reaches about 250° C., and an amount of the entrained water is used as a mark for determining that the reaction is ended. After the reaction is ended, the temperature is reduced, a saturated sodium carbonate aqueous solution is added for quenching reaction. Then, the temperature is increased to remove a low-boiling-point substance by reduced-pressure distillation, an inorganic solvent is filtered when it is hot, and an organic phase is washed for many times to obtain the product. The advantage of the process is that the whole process flow is relatively simple. The shortcomings are that the adopted reaction raw material p-dihydroxybenzene is expensive, limited in supply channel, and relatively unstable in cost; alkali liquor is required to be used to quench the Lewis acid and wash away metal ions catalyst remaining in the product, so that a great amount of waste water is produced; and the equipment is greatly corroded by the high reaction temperature and the acid medium.

Like the rubber antidegradant 3100, present synthesis processes for aryl substituted p-phenylenediamine substances all have problems of high cost, poor environment friendliness, high corrosiveness, and strict reaction condition. Therefore, it is necessary to provide a green preparation process for preparing an aryl substituted p-phenylenediamine substance, which is with the characteristics of low cost, high environment friendliness, mild reaction condition, relatively low corrosiveness to reaction equipment, and the like.

SUMMARY OF THE INVENTION

The present invention provides a method for preparing an aryl substituted p-phenylenediamine substance, so as to solve the problems of high cost, poor environment friendliness, high corrosiveness, and strict reaction condition when the aryl substituted p-phenylenediamine substance is synthesized in the conventional art.

In order to achieve the purpose, the present invention provides a method for preparing an aryl substituted p-phenylenediamine substance, and structural formula of the aryl substituted p-phenylenediamine substance is as follows:

where each of R' and R" is a phenyl or o-methylphenyl, and R' is the same as or different from the R"; and the preparation method comprises that: a raw material A and a raw material B are reacted in the presence of a hydrogen acceptor and a catalyst to form the aryl substituted p-phenylenediamine substance, the raw material A having a structure shown as Formula I, the raw material B being cyclohexanone and/or o-methylcyclohexanone, and the hydrogen acceptor being a hydrogen acceptor capable of accepting hydrogen for conversion into the raw material B,

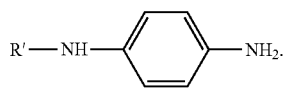

Formula I

Furthermore, in the present invention, the molar ratio of the raw material A and the raw material B is 20:1~5:1, and a molar ratio of the raw material A and the hydrogen acceptor is 1:10~1:2.5.

Furthermore, in the present invention, the hydrogen acceptor is a phenol and/or o-cresol.

Furthermore, in the present invention, the aryl substituted p-phenylenediamine substance is a rubber antidegradant 3100, and the preparation method comprises the following steps:

N-phenyl p-phenylenediamine is taken as the raw material A, the cyclohexanone and/or the o-methylcyclohexanone is taken as the raw material B, the phenol is taken as the hydrogen acceptor, and reaction is performed in the presence of the catalyst to obtain a first component; the N-phenyl p-phenylenediamine is taken as the raw material A, the cyclohexanone and/or the o-methylcyclohexanone is taken as the raw material B, the o-cresol is taken as the hydrogen acceptor, and reaction is performed in the presence of the catalyst, or, N-o-methylphenyl p-phenylenediamine is taken as the raw material A, the cyclohexanone and/or the o-methylcyclohexanone is taken as the raw material B, the phenol is taken as the hydrogen acceptor, and reaction is performed in the presence of the catalyst to obtain a second component; the N-o-methylphenyl p-phenylenediamine is taken as the raw material A, the cyclohexanone and/or the o-methylcyclohexanone is taken as the raw material B, the o-cresol is taken as the hydrogen acceptor, and reaction is performed in the presence of the catalyst to obtain a third component; and the first component, the second component, and the third component are mixed to obtain the rubber antidegradant 3100.

Furthermore, in the present invention, the aryl substituted p-phenylenediamine substance is the rubber antidegradant 3100, and the preparation method comprises the following steps: a mixture of the N-phenyl p-phenylenediamine and the N-o-methylphenyl p-phenylenediamine is taken as the raw material A, the cyclohexanone and/or the o-methylcyclohexanone are/is taken as the raw material B, a mixture of the phenol and the o-cresol is taken as the hydrogen acceptor, and reaction is performed in the presence of the catalyst to obtain the rubber antidegradant 3100.

Furthermore, in the present invention, the catalyst is a supported noble metal catalyst, and is preferably a Pd-C and/or Pt-C supported noble metal catalyst.

Furthermore, in the present invention, a using amount of the catalyst is 0.1~2% of a weight of the raw material A.

Furthermore, in the present invention, the raw material A and the raw material B are reacted for reaction time of 6~8 h under a temperature condition of 220~280° C.

Furthermore, in the present invention, after reaction of the raw material A and the raw material B in the presence of the hydrogen acceptor and the catalyst is finished, the preparation method further comprises that: reaction liquid obtained by the reaction is filtered to obtain filtrate, and reduced-pressure distillation is performed on the filtrate to obtain the aryl substituted p-phenylenediamine substance.

Furthermore, in the present invention, the raw material A and the raw material B are reacted in a nitrogen atmosphere.

With application of the technical solution of the present invention, the raw material A with the structure shown as Formula I is reacted with the cyclohexanone and/or the o-methylcyclohexanone to generate the aryl substituted p-phenylenediamine substance. Specifically, the cyclohexanone and the o-methylcyclohexanone both may undergo dehydrogenation reaction in the presence of the catalyst, and meanwhile, a hydrogen atom on amino at an N' position in the raw material A is substituted to form the aryl substituted p-phenylenediamine substance of which the R" is the phenyl or the o-methylphenyl. In addition, in the presence of the catalyst, the hydrogen acceptor in a reaction system continuously accepts hydrogen released from the cyclohexanone and/or the o-methylcyclohexanone to further form the raw material B to supply the cyclohexanone and/or o-methylcyclohexanone required by the reaction. In the preparation method, addition of the raw material B may be very small, and it is mainly taken as a primer raw material for the reaction. The raw material B may provide the required hydrogen for the hydrogen acceptor when being reacted with the raw material A in the presence of the catalyst, and a large amount of aryl substituted p-phenylenediamine substance is formed in processes of continuous hydrogen accepting of the hydrogen acceptor and continuous dehydrogenation of the generated compound B. According to the preparation method, the raw materials are low in cost and readily available, and a large amount of water is avoided to use for post-treatment of the reaction. Moreover, a reaction condition is relatively mild, and corrosion to reaction equipment is avoided. Therefore, the preparation method is environment-friendly and less in pollution, and may achieve better economic benefits.

DETAILED DESCRIPTION OF THE INVENTION AND EMBODIMENTS

It is important to note that embodiments in the application and characteristics in the embodiments may be combined without conflicts. The present invention is described below in combination with the examples in details.

As described in the Background, existing synthesis processes for aryl substituted p-phenylenediamine substances all have the problems of high cost, poor environment friendliness, high corrosiveness, and complex process. In order to solve these problems, the present invention provides a method for preparing an aryl substituted p-phenylenediamine substance, a structural formula of the aryl substituted p-phenylenediamine substance being as follows:

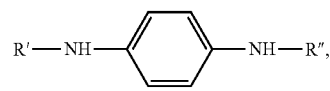

where each of R' and R" is phenyl or o-methylphenyl, and R' is the same as or different from the R"; and the preparation method comprises that: a raw material A and a raw material B are reacted in the presence of a hydrogen acceptor and a catalyst to form the aryl substituted p-phenylenediamine substance, the raw material A having a structure shown as Formula I, the raw material B being cyclohexanone and/or o-methylcyclohexanone, and the hydrogen acceptor being a hydrogen acceptor capable of accepting hydrogen for conversion into the raw material B,

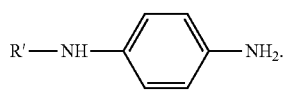

Formula I

According to the preparation method of the present invention, the raw material A with the structure shown as Formula I is reacted with the raw material B (cyclohexanone and/or o-methylcyclohexanone) to generate the aryl substituted p-phenylenediamine substance. Specifically, the cyclohexanone and the o-methylcyclohexanone both may undergo dehydrogenation reaction in the presence of the catalyst, and meanwhile, a hydrogen atom on amino at an N' position in the raw material A is substituted to form the aryl substituted p-phenylenediamine substance of which R" is the phenyl or the o-methylphenyl. In addition, the hydrogen acceptor in a reaction system continuously accepts hydrogen released from the cyclohexanone and/or the o-methylcyclohexanone in the presence of the catalyst to further form the raw material B to supply the cyclohexanone and/or o-methylcyclohexanone required by the reaction. In the preparation method, addition of the raw material B may be very small, it is mainly taken as a primer raw material for the reaction, and may provide the required hydrogen for the hydrogen acceptor when being reacted with the raw material in the presence of the catalyst, and a large amount of aryl substituted p-phenylenediamine substance is formed in processes of continuous hydrogen accepting of the hydrogen acceptor and continuous dehydrogenation of the generated compound B.

According to the preparation method of the present invention, the raw materials are low in cost and readily available, and use of a large amount of water for post-treatment of the reaction is avoided. Moreover, the reaction condition is relatively mild, and corrosion to reaction equipment is avoided. Therefore, the preparation method is environment-friendly and less polluting, and may achieve better economic benefits.

It is important to note that the aryl substituted p-phenylenediamine substance may be a compound or a mixture. When the adopted raw material A is a single structured compound and the raw material B is the cyclohexanone or the o-methylcyclohexanone, the prepared aryl substituted p-phenylenediamine substance is also a single structured compound. When the adopted raw material A, raw material B, or both, are a mixture of multiple compounds, the reaction may still be performed, and the obtained aryl substituted p-phenylenediamine substance is a mixture formed by two or more than two compounds with the same parent nucleus structure but different substituted aryl. Specifically, one skilled in the art may select different raw materials to be matched to obtain different aryl substituted p-phenylenediamine substances.

In the preparation method of the present invention, raw material B may be added in a very small amount so that it may provide the required hydrogen for the hydrogen acceptor when being reacted with the raw material A in the presence of the catalyst, and a large amount of aryl substituted p-phenylenediamine substance is formed in the processes of continuous hydrogen accepting of the hydrogen acceptor and continuous dehydrogenation of the generated compound B. In a preferred embodiment, a molar ratio of the raw material A and the raw material B is 20:1~5:1, and a molar ratio of the raw material A and the hydrogen acceptor is 1:10~1:2.5. Controlling the relationship between amount of each raw material within the above-mentioned range may effectively ensure a reaction rate and sufficient hydrogen in the reaction system and continuously convert the hydrogen acceptor into the raw material B for further reaction with the raw material A. Meanwhile, the raw material B which is relatively high in cost may further be saved, so that the preparation method is endowed with higher economy.

In a preferred embodiment, the hydrogen acceptor is phenol and/or o-cresol. The phenol and the o-cresol have higher conversion efficiency when accepting hydrogen for conversion into the cyclohexanone and the o-methylcyclohexanone, and meanwhile, the two hydrogen acceptors are relatively low in cost and more suitable to be used for industrial production in large doses.

As long as the preparation method provided by the present invention is adopted, the aryl substituted p-phenylenediamine substance with a specific structure may be prepared. In a preferred embodiment, the aryl substituted p-phenylenediamine substance is Rubber antidegradant 3100, and the preparation method comprises the following steps: N-phenyl p-phenylenediamine is taken as the raw material A, the cyclohexanone and/or the o-methylcyclohexanone is taken as the raw material B, the phenol is taken as the hydrogen acceptor, and reaction is performed in the presence of the catalyst to obtain a first component (as mentioned above, the addition of the raw material B may be in very small amount, it may provide the required hydrogen for the hydrogen acceptor when being reacted with the raw material A in the presence of the catalyst, and a large amount of aryl substituted p-phenylenediamine substance is formed in the processes of continuous hydrogen accepting of the hydrogen acceptor and continuous dehydrogenation of the generated compound B. In this process, although the cyclohexanone and/or the o-methylcyclohexanone are/is taken as the raw material B, since the addition is relatively small, a main component of a final product is still the first component); the N-phenyl p-phenylenediamine is taken as the raw material A, the cyclohexanone and/or the o-methylcyclohexanone is taken as the raw material B, the o-cresol is taken as the hydrogen acceptor, and reaction is performed in the presence of the catalyst, or, N-o-methylphenyl p-phenylenediamine is taken as the raw material A, the cyclohexanone and/or the o-methylcyclohexanone is taken as the raw material B, the phenol is taken as the hydrogen acceptor, and reaction is performed in the presence of the catalyst to obtain a second component (similarly, in this process, although the cyclohexanone and/or the o-methylcyclohexanone are/is taken as the raw material B, since the addition is relatively small, a main component of a final product is still the second component); the N-o-methylphenyl p-phenylenediamine is taken as the raw material A, the cyclohexanone and/or the o-methylcyclohexanone is taken as the raw material B, the o-cresol is taken as the hydrogen acceptor, and reaction is performed in the presence of the catalyst to obtain a third component (similarly, although the cyclohexanone and/or the o-methylcyclohexanone is taken as the raw material B, a main component of product generated by the step is still the third component); and the first component, the second component and the third component are mixed to obtain the rubber antidegradant 3100.

There is no particular order for the steps of preparing the first, second, and third components in the method of the present invention. As one skilled in the art knows, the rubber antidegradant 3100 is a mixture of three aryl substituted p-phenylenediamine compounds, and actually, in the preparation steps, the single raw material A, raw material B and hydrogen acceptor are adopted to prepare the three components, and the three components are finally mixed to obtain the rubber antidegradant 3100. In a mixing process, one skilled in the art are only required to set respective using amounts of the three components according to a predetermined requirement of the rubber antidegradant 3100.

Of course, besides the abovementioned sub-steps for preparing the rubber antidegradant 3100, a one-step method may also be adopted to prepare the rubber antidegradant 3100, and the preparation method comprises the following steps: a mixture of the N-phenyl p-phenylenediamine and the N-o-methylphenyl p-phenylenediamine is taken as the raw material A, the cyclohexanone and/or the o-methylcyclohexanone is taken as the raw material B, a mixture of the phenol and the o-cresol is taken as the hydrogen acceptor, and reaction is performed in the presence of the catalyst to obtain the rubber antidegradant 3100. Preparing the rubber antidegradant 3100 with such an one-step method may further simplify reaction procedures and reduce reaction cost.

In the preparation method of the present invention, the adopted catalyst is only required to have dehydrogenation and hydrogenation functions. In a preferred embodiment, the catalyst is a supported noble metal catalyst, and preferably, a Pd-C and/or Pt-C supported noble metal catalyst. These catalysts have relatively high catalytic activity, and may make the reaction condition milder. In addition, one skilled in the art may regulate a specific amount of the catalyst used in the reaction. In a preferred embodiment, the amount of the catalyst used in the reaction is 0.1~2% by weight of the raw material A.

As mentioned above, due to a unique reaction principle and route in the present invention, the synthesis condition for the aryl substituted p-phenylenediamine substance is milder. In a preferred embodiment, the raw material A and the raw material B are reacted for reaction time of 6~8 hours under a temperature condition of 220~280° C. Controlling the temperature and time of the reaction system within the above-mentioned ranges may increase the conversion rate and the speed and is also favorable for reducing the side reaction rate and endowing the product with higher purity.

More preferably, after reaction of the raw material A and the raw material B in the presence of the hydrogen acceptor and the catalyst is finished, reaction liquid obtained by the reaction is filtered to obtain filtrate, and reduced-pressure distillation is performed on the filtrate to obtain the aryl substituted p-phenylenediamine substance. Due to the unique reaction route during the reaction, a post-treatment process is relatively simple. Furthermore, the raw material A and the raw material B are preferably reacted in a nitrogen atmosphere.

The application are further described below in combination with specific examples in details, and these examples should not be understood to limit the scope of protection of the application.

Example 1

36.8 g (0.2 mol) of N-phenyl p-phenylenediamine, 94.1 g (1 mol) of phenol, 2.0 g (0.02 mol) of cyclohexanone and 1.3 g of dry Pd/C (containing 5 wt % Pd) catalyst are added into a 500 mL autoclave; and stirring is started, heating is performed to increase a temperature to 220° C. after nitrogen displacement is performed for 3 times, heat is preserved to perform reaction for 6 h, the temperature is reduced to a room temperature for discharging, filtering is performed, the catalyst is recovered, reduced-pressure distillation is performed on filtrate to remove unreacted phenol and cyclohexanone to obtain 51.7 g of distillation residual liquid, sampling is performed to measure the content of N,N'-diphenyl p-phenylenediamine to be 94.1%, and the yield is calculated to be 93.6%.

Examples 2 to 5

The same raw materials and process conditions in Example 1 are adopted to prepare N,N'-diphenyl p-phenylenediamine, and differences are differences in relationships between using amounts of each raw material (wherein a weight of the N-phenyl p-phenylenediamine is kept unchanged). Specific relationships between the using amounts and product conditions are as follows:

| Example | Molar ratio of N-phenyl p-phenylenediamine and cyclohexanone | Molar ratio of N-phenyl p-phenylenediamine and phenol | Weight percent of the catalyst in N-phenyl p-phenylenediamine | Product content (%) | Yield (%) |
| --- | --- | --- | --- | --- | --- |
| 2 | 5:1 | 1:2.5 | 0.1% | 67.5 | 75.1 |
| 3 | 10:1 | 1:5 | 0.5% | 68 | 75.1 |
| 4 | 15:1 | 1:7.5 | 1% | 68.3 | 79.6 |
| 5 | 20:1 | 1:10 | 2% | 80.4 | 89.7 |

Example 6

36.8 g (0.2 mol) of N-phenyl p-phenylenediamine, 108.1 g (1 mol) of o-cresol, 2.0 g (0.02 mol) of cyclohexanone and 1.3 g of dry Pt/C (containing 5 wt % Pt) catalyst are added into a 500 mL autoclave; and stirring is started, heating is performed to increase a temperature to 250° C. after nitrogen displacement is performed for 3 times, heat is preserved to perform reaction for 6 h, the temperature is reduced to a room temperature for discharging, filtering is performed, the catalyst is recovered, reduced-pressure distillation is performed on filtrate to remove unreacted o-cresol and cyclohexanone to obtain 49.7 g of distillation residual liquid, sampling is performed to measure the content of N-phenyl-N'-methylphenyl p-phenylenediamine to be 68%, and the yield is calculated to be 90.8%.

Example 7

39.6 g (0.2 mol) of N-methylphenyl p-phenylenediamine, 94.1 g (1 mol) of phenol, 2.0 g (0.02 mol) of cyclohexanone and 1.3 g of dry Pd/C (containing 5 wt % Pd) catalyst are added into a 500 mL autoclave; and stirring is started, heating is performed to increase a temperature to 250° C. after nitrogen displacement is performed for 3 times, heat is preserved to perform reaction for 6 h, the temperature is reduced to a room temperature for discharging, filtering is performed, the catalyst is recovered, reduced-pressure distillation is performed on filtrate to remove unreacted phenol and cyclohexanone to obtain 53.7 g of distillation residual liquid, sampling is performed to measure the content of N-phenyl-N'-methylphenyl p-phenylenediamine to be 93.8%, and the yield is calculated to be 91.9%.

Example 8

39.6 g (0.2 mol) of N-methylphenyl p-phenylenediamine, 108.1 g (1 mol) of o-cresol, 2.0 g (0.02 mol) of cyclohexanone and 1.3 g of dry Pd/C (containing 5 wt % Pd) catalyst are added into a 500 mL autoclave; and stirring is started, heating is performed to increase a temperature to 270° C. after nitrogen displacement is performed for 3 times, heat is preserved to perform reaction for 6 h, the temperature is reduced to room temperature for discharging, filtering is performed, the catalyst is recovered, reduced-pressure distillation is performed on filtrate to remove unreacted o-cresol and cyclohexanone to obtain 56.6 g of distillation residual liquid, sampling is performed to measure the content of N,N'-di(methylphenyl) p-phenylenediamine to be 93.4%, and the yield is calculated to be 91.8%.

Example 9

18.4 g (0.1 mol) of N-phenyl p-phenylenediamine, 19.8 g (0.1 mol) of N-methylphenyl p-phenylenediamine, 94.1 g (1 mol) of phenol, 2.0 g (0.02 mol) of cyclohexanone and 1.3 g of dry Pd/C (containing 5 wt % Pd) catalyst are added into a 500 mL autoclave; and stirring is started, heating is performed to increase a temperature to 250° C. after nitrogen displacement is performed for 3 times, heat is preserved to perform reaction for 6 h, the temperature is reduced to a room temperature for discharging, filtering is performed, the catalyst is recovered, reduced-pressure distillation is performed on filtrate to remove unreacted phenol and cyclohexanone to obtain 52 g of distillation residual liquid, sampling is performed to measure contents of N,N'-diphenyl p-phenylenediamine and N-phenyl-N'-methylphenyl p-phenylenediamine to be 47.2% and 46.8% respectively, and yields are calculated to be 94.4% and 88.8% respectively.

Example 10

18.4 g (0.1 mol) of N-phenyl p-phenylenediamine, 19.8 g (0.1 mol) of N-methylphenyl p-phenylenediamine, 108.1 g (1 mol) of o-cresol, 2.0 g (0.02 mol) of cyclohexanone and 1.3 g of dry Pd/C (containing 5 wt % Pd) catalyst are added into a 500 mL autoclave; and stirring is started, heating is performed to increase a temperature to 270° C. after nitrogen displacement is performed for 3 times, heat is preserved to perform reaction for 8 h, the temperature is reduced to a room temperature for discharging, filtering is performed, the catalyst is recovered, reduced-pressure distillation is performed on filtrate to remove unreacted phenol and cyclohexanone to obtain 54.2 g of distillation residual liquid, sampling is performed to measure contents of N-phenyl-N'-methylphenyl p-phenylenediamine and N,N'-di(methylphenyl) p-phenylenediamine and to be 47.3% and 47.2% respectively, and yields are calculated to be 93.6% and 88.8% respectively.

Example 11

18.4 g (0.1 mol) of N-phenyl p-phenylenediamine, 19.8 g (0.1 mol) of N-methylphenyl p-phenylenediamine, 47.1 g (0.5 mol) of phenol, 54.1 g (0.5 mol) of o-cresol, 2.0 g (0.02 mol) of cyclohexanone and 1.3 g of dry Pd/C (containing 5 wt % Pd) catalyst are added into a 500 mL autoclave; and stirring is started, heating is performed to increase a temperature to 270° C. after nitrogen displacement is performed for 3 times, heat is preserved to perform reaction for 8 h, the temperature is reduced to a room temperature for discharging, filtering is performed, the catalyst is recovered, reduced-pressure distillation is performed on filtrate to remove unreacted phenol and cyclohexanone to obtain 53.4 g of distillation residual liquid, sampling is performed to measure contents of N,N'-diphenyl p-phenylenediamine, N-phenyl-N'-methylphenyl p-phenylenediamine and N,N'-di(methylphenyl) p-phenylenediamine to sequentially be 42.2%, 37.5% and 14.1%, and this product may directly be used as a rubber antidegradant 3100.

Example 12

27.6 g (0.15 mol) of N-phenyl p-phenylenediamine, 9.9 g (0.05 mol) of N-methylphenyl p-phenylenediamine, 23.5 g (0.25 mol) of phenol, 81.1 g (0.75 mol) of o-cresol, 2.0 g (0.02 mol) of cyclohexanone and 1.3 g of dry Pd/C (containing 5 wt % Pd) catalyst are added into a 500 mL autoclave; and stirring is started, heating is performed to increase a temperature to 280° C. after nitrogen displacement is performed for 3 times, heat is preserved to perform reaction for 8 h, the temperature is reduced to a room temperature for discharging, filtering is performed, the catalyst is recovered, reduced-pressure distillation is performed on filtrate to remove unreacted phenol and cyclohexanone to obtain 54.5 g of distillation residual liquid, sampling is performed to measure contents of N,N'-diphenyl p-phenylenediamine, N-phenyl-N'-methylphenyl p-phenylenediamine and N,N'-di(methylphenyl) p-phenylenediamine to sequentially be 22.6%, 43.7% and 24.2%, and this product may directly be used as a rubber antidegradant 3100.

From the above examples, the present invention achieve the following technical effects:

According to the preparation method, the raw materials are low in cost and readily available, and use of a large amount of water for post-treatment of the reaction is avoided. Moreover, the reaction condition is relatively mild, and corrosion to reaction equipment is avoided. Therefore, the preparation method is environment-friendly and less in pollution, and may achieve better economic benefits. More particularly, controlling a proportion of each raw material and the reaction process condition may further increase the product content and yield of the product.

The above is only preferred embodiments of the present invention and not intended to limit the present invention. For one skilled in the art, the present invention may further have various modifications and variations. Any modifications, equivalent replacements, improvements and the like made within the spirit and principle of the present invention shall fall within the scope of protection of the present invention.

We claim:

1. A method for preparing one or more aryl substituted p-phenylenediamine compounds selected from the group consisting of N,N'-diphenyl-p-phenylenediamine and N-o-methylphenyl-N'-phenyl-p-phenylenediamine, comprising
reacting a reaction system consisting of nitrogen gas, a raw material A, a primer material, and a hydrogen acceptor in the presence of a supported noble metal catalyst to form the one or more aryl substituted p-phenylenediamine compounds,
wherein the raw material A is N-phenyl-p-phenylenediamine, N-o-methylphenyl-p-phenylenediamine, or both; the primer material is o-methylcyclohexanone; the hydrogen acceptor is phenol; and a molar ratio of the raw material A to the primer material at the beginning of the reaction is 1:0.05 to 1:0.2.

2. A method for preparing one or more aryl substituted p-phenylenediamine compounds selected from the group consisting of N,N'-di(o-methylphenyl)-p-phenylenediamine and N-o-methylphenyl-N'-phenyl-p-phenylenediamine, comprising reacting a reaction system consisting of nitrogen gas, a raw material A, a primer material, and a hydrogen acceptor in the presence of a supported noble metal catalyst to form the aryl substituted p-phenylenediamine compounds selected from the group consisting of N,N'-di(o-methylphenyl)-p-phenylenediamine and N-o-methylphenyl-N'-phenyl-p-phenylenediamine, wherein the raw material A is N-phenyl-p-phenylenediamine, N-o-methylphenyl-p-phenylenediamine, or both; the primer material is cyclohexanone; the hydrogen acceptor is o-cresol; and a molar ratio of the raw material A to the primer material at the beginning of the reaction is 1:0.05 to 1:0.2.

3. The method as claimed in claim 1, wherein the amount of the catalytic noble metal used in the reaction is 0.1% to 2% by weight of the raw material A.

4. The method as claimed in claim 1, wherein the reaction system is reacted for 6 to 8 hours at a temperature of 220° C. to 280° C. to obtain a reaction liquid.

5. The method as claimed in claim 4, further comprising filtering the reaction liquid to obtain a filtrate after the reaction is finished, and performing reduced-pressure distillation on the filtrate to obtain the aryl substituted p-phenylenediamine compound.

6. The method as claimed in claim 2, wherein the amount of the catalytic noble metal used in the reaction is 0.1% to 2% by weight of the raw material A.

7. The method as claimed in claim 2, wherein the reaction system is reacted for 6 to 8 hours at a temperature of 220° C. to 280° C. to obtain a reaction liquid.

8. The method as claimed in claim 7, further comprising filtering the reaction liquid to obtain a filtrate after the reaction is finished, and performing reduced-pressure distillation on the filtrate to obtain the aryl substituted p-phenylenediamine compound.

* * * * *